(12) United States Patent
Morfill et al.

(10) Patent No.: US 8,926,920 B2
(45) Date of Patent: Jan. 6, 2015

(54) PLASMA SOURCE

(75) Inventors: Gregor Eugen Morfill, Munich (DE); Bernd Steffes, Garching (DE)

(73) Assignee: Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 522 days.

(21) Appl. No.: 12/598,988

(22) PCT Filed: May 2, 2008

(86) PCT No.: PCT/EP2008/003568
§ 371 (c)(1),
(2), (4) Date: Nov. 5, 2009

(87) PCT Pub. No.: WO2008/138504
PCT Pub. Date: Nov. 20, 2008

(65) Prior Publication Data
US 2010/0130911 A1  May 27, 2010

(30) Foreign Application Priority Data
May 15, 2007  (EP) .................................... 07009716

(51) Int. Cl.
*A61L 9/00* (2006.01)
*B01J 7/00* (2006.01)
*H05H 1/24* (2006.01)
*H05H 1/34* (2006.01)
*A61L 2/00* (2006.01)

(52) U.S. Cl.
CPC . *H05H 1/24* (2013.01); *H05H 1/34* (2013.01); *H05H 2001/3484* (2013.01)
USPC ........................ 422/305; 422/292; 422/306

(58) Field of Classification Search
CPC .................................... H05H 1/26; A61L 2/14
USPC .................................... 422/22, 292, 305, 306
See application file for complete search history.

(56) References Cited

U.S. PATENT DOCUMENTS

| 2,922,869 | A | * | 1/1960 | Giannini et al. | ................. | 219/75 |
| 3,692,431 | A |   | 9/1972 | Gebel |   |   |
| 4,197,610 | A | * | 4/1980 | Schneider | ........................ | 15/383 |
| 4,707,210 | A | * | 11/1987 | Misumi | .................... | 156/345.43 |

(Continued)

FOREIGN PATENT DOCUMENTS

| FR | 1376216 | | 12/1964 |
| GB | 1066399 | A * | 4/1967 |

(Continued)

OTHER PUBLICATIONS

English translation of JP 2003024426, Jan. 2003.*

(Continued)

*Primary Examiner* — Regina M Yoo
(74) *Attorney, Agent, or Firm* — Caesar, Rivise, Bernstein, Cohen & Pokotilow, Ltd.

(57) ABSTRACT

The invention relates to a plasma source (1) comprising: a conduit (3, 4) carrying a gas flow and an ionization chamber (10) in which a plasma is generated, wherein the ionization chamber (10) is connected to the conduit (3, 4), so that the gas flow in the conduit (3, 4) carries away gas particles out of the ionization chamber (10) thereby reducing the pressure in the ionization chamber (10).

33 Claims, 18 Drawing Sheets

(56) References Cited

U.S. PATENT DOCUMENTS

| | | | |
|---|---|---|---|
| 4,846,101 A * | 7/1989 | Montgomery et al. | 118/723 E |
| 5,296,672 A | 3/1994 | Ramakrishnan et al. | |
| 5,399,833 A * | 3/1995 | Camacho | 219/121.59 |
| 5,573,682 A | 11/1996 | Beason, Jr. et al. | |
| 6,114,649 A | 9/2000 | Delcea | |
| 6,121,569 A | 9/2000 | Miley et al. | |
| 6,320,156 B1 | 11/2001 | Yamaguchi et al. | |
| 6,455,014 B1 | 9/2002 | Hammerstrom et al. | |
| 7,011,790 B2 | 3/2006 | Ruan et al. | |
| 2003/0012689 A1* | 1/2003 | Caputo et al. | 422/32 |
| 2004/0265167 A1* | 12/2004 | Morrison | 422/33 |
| 2005/0208614 A1* | 9/2005 | Kline et al. | 435/34 |
| 2005/0258149 A1* | 11/2005 | Glukhoy et al. | 219/121.48 |
| 2006/0263275 A1* | 11/2006 | Lobach | 422/186 |
| 2007/0021748 A1 | 1/2007 | Suslov | |

FOREIGN PATENT DOCUMENTS

| | | | | |
|---|---|---|---|---|
| GB | 1274876 A | * | 5/1972 | |
| JP | 0355410 A | | 3/1991 | |
| JP | 2003024426 | * | 1/2003 | A61L 9/015 |
| JP | 2005126737 A | | 5/2005 | |
| JP | 20075059 A | | 1/2007 | |
| WO | 2005026650 A2 | | 3/2005 | |
| WO | 2007006516 A2 | | 1/2007 | |
| WO | 2007031250 A1 | | 3/2007 | |

OTHER PUBLICATIONS

Stoffels "The healing touch of a micro-plasma—Development of a low-power discharge for fine medical treatment", http://www.phys.tue.nl/EPG/epghome/projects/bmtweb.htm (2009).

International Search Report for PCT/EP2008/003568.

English-language Patent Abstract for JP 03-055410, (Mar. 11, 1991).

English-language Patent Abstract for JP 2005126737, (May 19, 2005).

English-language Patent Abstract for JP 2007005059, (Jan. 11, 2007).

English-language translation of Apr. 10, 2013 Office Action issued by JPO for counterpart Japanese Patent Application No. 2010-507823.

* cited by examiner

PLASMA SOURCE

FIELD OF THE INVENTION

The invention relates to a plasma source, particularly for the disinfection of wounds.

BACKGROUND OF THE INVENTION

The use of non-equilibrium plasmas for the invivo sterilization of wounds has been discussed in Stoffels, E.; Stoffels, W.: "The healing touch of a micro-plasma", published on http://www.phys.tue.nl. However, the invivo sterilization of wounds requires low temperatures of the plasma and a low electromagnetic irradiation, so that the conventional plasma sources are not suitable for the invivo sterilization of wounds.

Further, WO 2007/031250 A1 discloses a plasma source which is suitable for the aforementioned invivo sterilization of wounds.

High-temperature plasma sources are disclosed, for example, in US 2007/0021748 A1, U.S. Pat. No. 5,573,682, U.S. Pat. No. 5,296,672, FR 1 376 216, U.S. Pat. No. 6,114,649 and U.S. Pat. No. 6,121,569. Other types of conventional plasma sources are disclosed in WO 2005/026650 A2 and U.S. Pat. No. 3,692,431. However, these plasma sources are not suitable for the invivo sterilization of wounds which requires a low temperature plasma.

SUMMARY OF THE INVENTION

Therefore, it is a general object of the invention to improve the plasma generation within a plasma source which is suitable for the invivo sterilization of wounds.

This object is achieved by a plasma source according to the invention.

According to the invention, a plasma source is provided comprising an ionization chamber in which a plasma is generated. Further, the plasma source comprises a conduit carrying a gas flow of a carrier gas (e.g. ambient air, argon or nitrogen). The plasma source according to the invention is characterized in that the ionization chamber is connected to the conduit, so that the gas flow in the conduit carries away gas particles (e.g. ions, electrons, atoms) out of the ionization chamber thereby reducing the pressure in the ionization chamber. The pressure reduction in the ionization chamber advantageously yields an improvement in the efficiency of the plasma generation since the ionizability of gases generally declines with a rising pressure. Therefore, it is easier and more efficient to generate a plasma in a gas having a low pressure.

In a preferred embodiment of the invention, the conduit carrying the gas flow comprises a nozzle, wherein the ionization chamber is connected to the conduit downstream the nozzle. In this embodiment, the pressure reduction within the ionization chamber is produced by the gas flow in the conduit downstream the nozzle.

Preferably, the nozzle is a Venturi nozzle or a Laval nozzle. When using a Laval nozzle, the nozzle generates a shock wave within the carrier gas flow thereby increasing the flow speed of the carrier gas flow at the junction connecting the ionization chamber to the conduit, which in turn results in a pressure reduction. However, it should be noted that the invention is not restricted to the aforementioned types of nozzles.

However, it should be noted that the nozzle is preferably shaped in such way that the gas flow in the conduit comprises a subsonic flow speed (M<1) upstream the nozzle, a supersonic flow speed (M>1) downstream nozzle and/or a substantially sonic flow speed (M≈1) in the nozzle. Such a distribution of the flow speeds along the conduit produces the desired pressure reduction in the supersonic gas flow in the conduit according to the well-known laws of Bernoulli.

In a preferred embodiment of the invention, the ionization chamber is ring-shaped and surrounds the conduit. In this embodiment, the nozzle and the surrounding ionization chamber can be arranged in the same cross sectional plain. Alternatively, it is possible that the ionization chamber is axially displaced with regard to the nozzle. Preferably, the ionization chamber is displaced axially in flow direction relative to the nozzle of the conduit carrying the gas flow. In other words, the ionization chamber is preferably arranged downstream then nozzle. Therefore, the junction of the ionization chamber and the conduit is located downstream the nozzle, where the pressure is reduced as explained above.

In another embodiment of the invention, the ionization chamber is cup-shaped and open in flow direction, wherein the ionization chamber is disposed within the conduit, particularly within the nozzle. In this embodiment, the cup-shaped ionization chamber and the surrounding conduit (e.g. the nozzle) are preferably arranged coaxially, so that the gas flow in the conduit flows in the ring-shaped gap between the inner wall of the nozzle and the outer surface of the cup-shaped ionization chamber. Then, the gas flow in the ring-shaped gap passes the ionization chamber and carries away gas particles out of the interior of the ionization chamber thereby reducing the pressure within the ionization chamber.

In the aforementioned embodiment, the cup-shaped ionization chamber preferably touches the inner surface of the nozzle at the downstream end of the ionization chamber thereby closing the aforementioned ring-shaped gap between the inner surface of the nozzle and the outer surface of the cup-shaped ionization chamber. However, the cup-shaped ionization chamber preferably comprises axially arranged notches at the ring-shaped contact point between the ionization chamber and the nozzle, so that the gas flow in the ring-shaped gap between the inner surface of the nozzle and the outer surface of the ionization chamber can flow through these notches.

Further, the cup-shaped ionization chamber preferably comprises an axial position, which is adjustable in axial direction, i.e. the cup-shaped ionization chamber can be adjusted axially relative to the surrounding conduit.

Further, the plasma source according to the invention preferably comprises a first electrode and a second electrode for generating the plasma in the ionization chamber. However, the invention is not restricted to electrode arrangements comprising two electrodes for plasma generation. It is also possible to use electrode arrangements comprising more than two electrodes as disclosed in WO 2007/031250 A1, which is therefore incorporated by a reference herein.

In a preferred embodiment of the invention, the first electrode is formed by the nozzle, whereas the second electrode is formed by a conic part of the conduit, wherein the conic part of the conduit is tapering in flow direction and surrounding the nozzle as already mentioned above. In this embodiment of the invention, the nozzle empties into the funnel-shaped conic part of the conduit.

In another embodiment of the invention, the first electrode and the second electrode are both disposed within the ionization chamber. Such an electrode arrangement is preferred in the aforementioned embodiment comprising a cup-shaped ionization chamber.

In yet another embodiment of the invention, the first electrode is formed by the conduit, particularly by the nozzle, whereas the second electrode is disposed alone within the ionization chamber. In this embodiment, electrical discharges take place between the inner surface of the conduit on the one hand and the second electrode in the ionization chamber on the other hand. Therefore, different electrical potentials are applied to the conduit on the one hand and to the second electrode in the ionization chamber on the other hand. For example, the conduit can be electrically grounded, whereas a positive or negative high voltage potential is applied to the second electrode in the ionization chamber.

The plasma generation within the ionization chamber generally produces radio frequency (RF) radiation or microwaves, which can be shielded by the walls of the ionization chamber or by the walls of the surrounding conduit in order to reduce RF or microwave irradiation of the plasma source. Further, it is possible to encase the plasma source by a housing made from an electrically conductive material in order to reduce the RF or microwave irradiation.

Further, the plasma source according to the invention can be configured in such a way that there is no direct radiation path from the inside of the ionization chamber into the conduit carrying the gas flow and through the outlet of the conduit, so that the plasma source is substantially free of plasma generated electro magnetic irradiation, e.g. ultraviolet irradiation.

However, in some applications of a plasma source ultraviolet irradiation might be desirable, e.g. for sterilization of wounds or for decontamination of surfaces. Therefore, it is also possible that the plasma source according to the invention is configured in such a way that there is a direct radiation path from the inside of the ionization chamber into the conduit carrying the gas flow and through the outlet of the conduit, so that the plasma source emits plasma generated electromagnetic irradiation.

Further, the ionization chamber may comprise walls, which are at least partially transparent thereby enabling a visual control of the plasma generation within the ionization chamber. For example, a window can be disposed in the walls of the ionization chamber and/or in the walls of the surrounding conduits so that the plasma generation in the ionization chamber can be visually monitored through the window, which is therefore preferably transparent for visible light and in-transparent for ultraviolet light. Further, a photo diode, a CCD camera (CCD: Charge coupled device) or any other optical sensor can be used for monitoring the plasma generation through the window.

It should further be noted that the ionization chamber may comprise a connection for connecting a vacuum meter or the like.

In another embodiment of the invention, the plasma source comprises a magnet generating a magnetic field in the ionization chamber and/or downstream the ionization chamber in a conduit, wherein the magnetic field enhances the plasma generation. This is reasonable if the mean free path of the charge carriers (i.e. electrons) of the plasma is sufficient to produce a significant effect of the magnetic field on the charge carriers due to the Lorentz force.

It should further be mentioned that the conduit carrying the carrier gas flow comprises an inlet for introducing the gas flow into the conduit and an outlet for dispensing the gas flow with the intermixed plasma onto an object, which is to be treated with the plasma.

Further, the vacuum in the ionization chamber is preferably in the range between 5 mbar to 900 mbar and more preferably in the range between 400 mbar to 600 mbar. However, the invention is not restricted to the aforementioned pressure range.

Moreover, it should be noted that the gas flow introduced into the conduit preferably consists of ambient air, nitrogen, noble gas (e.g. argon) or one of the aforementioned gases with additives, particularly with carbon dioxide.

Further, the gas flow in the conduit preferably amounts to less than 50 l/min., 40 l/min., 30 l/min., 20 l/min., or even to less than 10 l/min. However, the invention is not restricted to the aforementioned limits for the gas flow in the conduit.

Further, the plasma source according to the invention preferably comprises a plasma generator driving the electrodes within the ionization chamber. In one embodiment of the invention the plasma generator produces a direct current (DC) excitation in the ionization chamber. In another embodiment, the plasma generator produces an alternating current (AC) excitation in the ionization chamber, particularly a radio frequency (RF) excitation.

It should further be noted that the plasma source according to the invention preferably generates a non-thermal plasma having a low temperature, so that the plasma can be used to treat wounds or other temperature sensitive surfaces. Therefore, the plasma generated by the plasma source preferably has a temperature of less than 100° C., 75° C., 50° C., 40° C. or even less than 30° C. measured at the outlet of the plasma source.

It has already been mentioned that the gas flow in the conduit carries away gas particles out of the ionization chamber thereby reducing the pressure within the ionization chamber. In the preferred embodiment of the invention, different types of gas particles are carried away out of the ionization chamber, e.g. gas molecules, gas atoms, gas ions and/or electrons.

It should further be noted that the invention is also directed to a medical device comprising a plasma source as mentioned above. For example, sterilizers or cauterizers may be equipped with the plasma source according to the invention.

Moreover, the invention is directed to a method of non-therapeutic use of a plasma source according to the invention for treatment of an object, which can be sterilized or decontaminated by the plasma.

The non-destructive decontamination of objects may be of interest in astronautics, e.g. when parts of a space craft shall be decontaminated after return to earth. Therefore, the plasma source according to the invention can be used to decontaminate electronic circuits, electric or electronic components, subassemblies of a space craft or the surface of a space-suit.

The invention and its particular features and advantages will become more apparent from the following detailed description considered with reference to the accompanying drawings.

DETAILED DESCRIPTION OF THE DRAWINGS

Figure 1:
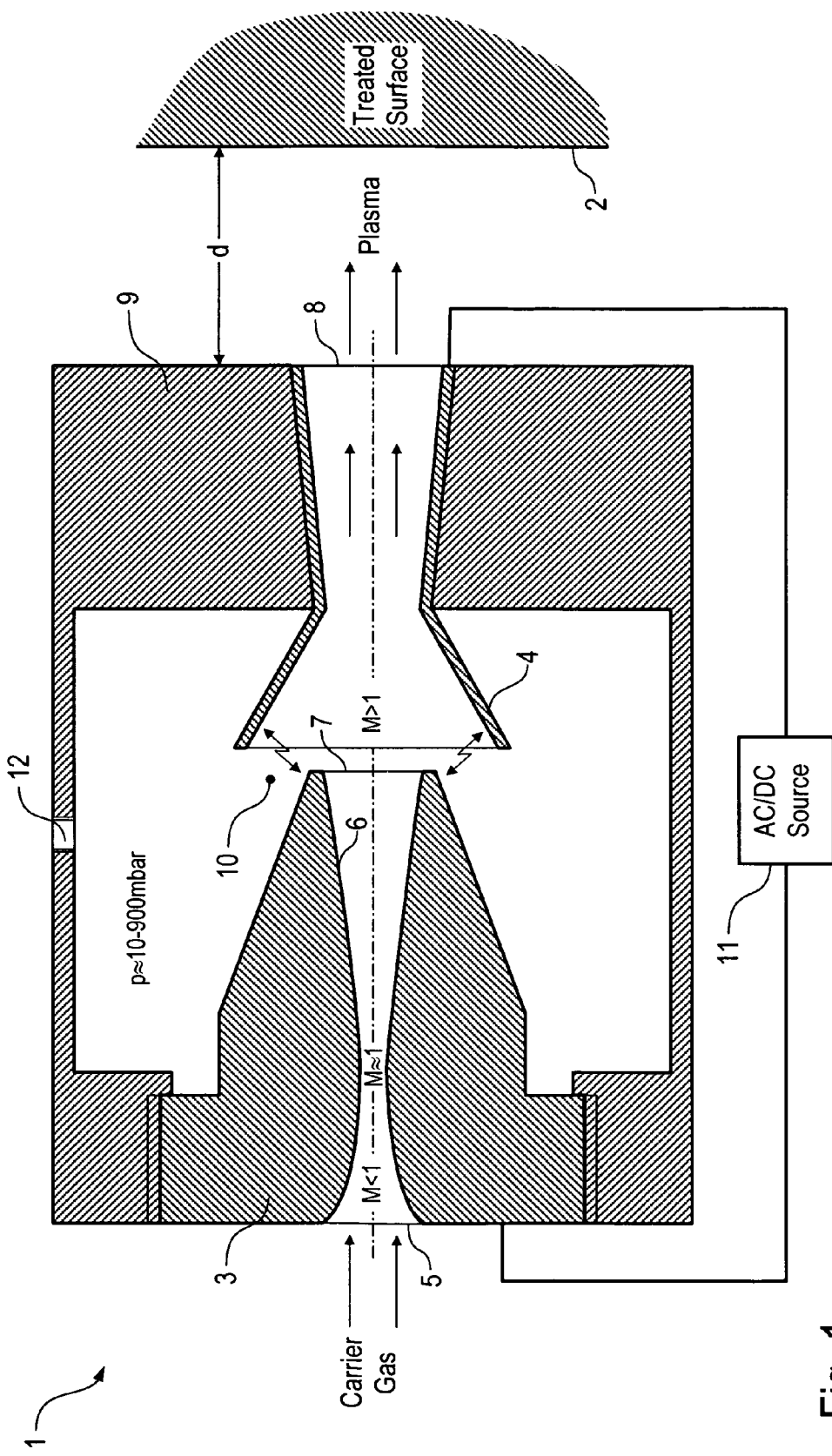
FIG. 1 is a sectional view of a plasma source according to the invention comprising a Laval nozzle and a funnel-shaped counter electrode.

FIG. 1 shows a sectional view of an embodiment of a plasma source 1 according to the invention, which can be used for plasma treatment of an object 2, e.g. a wound, which is to be sterilized.

The plasma source 1 comprises a conduit carrying a gas flow, wherein the conduit consists of a modified Laval nozzle 3 and a conduit pipe 4.

The Laval nozzle 3 is arranged upstream and comprises an inlet 5 for introducing a carrier gas flow into the plasma source 1. Further, the Laval nozzle 3 comprises an inner wall 6 which is shaped in such a way that the carrier gas flow within the Laval nozzle 3 comprises a subsonic flow speed (M<1) at the inlet 5, a supersonic flow speed (M>1) at an outlet 7 of the Laval nozzle 3 and a substantially sonic flow speed (M≈1) at a bottleneck within the Laval nozzle 3. Therefore, the gas pressure at the outlet 7 of the Laval nozzle 3 is reduced, which enhances the plasma generation, which will be described in detail later.

The conduit pipe 4 is disposed downstream behind the Laval nozzle 3 and comprises a funnel-shaped upstream portion and a cylindrically shaped downstream portion and an outlet 8 for applying the plasma to the surface of the object 2.

It should further be noted that there is an axial displacement between the Laval nozzle 3 and the conduit pipe 4, so that there is a gap between the Laval nozzle 3 and the conduit pipe 4, whereas the gas jet is flowing freely in the gap thereby generating a vacuum.

Further, the Laval nozzle 3 and the conduit pipe 4 are encased by a housing 9 defining an ionization chamber 10 between the Laval nozzle 3 and the conduit pipe 4 on the inside and the walls of the housing 9 on the outside.

The Laval nozzle 3 comprises an external thread, which is screwed with an internal thread of the housing 9.

Further, the cylindrical downstream portion of the conduit pipe 4 comprises an external thread, which is screwed with an internal thread of the housing 9.

In this embodiment, both the Laval nozzle 3 and the conduit pipe 4 consist of an electrically conductive material, whereas the housing 9 consists of an electrically non-conductive material.

The plasma source 1 further comprises a plasma generator 11, which can be an AC-source, a DC-source or an RF-source depending on the excitation mechanism used for plasma generation. The plasma generator 11 is connected to the Laval nozzle 3 and to the conduit pipe 4, so that electrical discharges take place in the ionization chamber 10 between the downstream end of the Laval nozzle 3 and the upstream end of the conduit pipe 4, which is illustrated in the drawings by arrows.

It has already been mentioned above that the supersonic flow speed (M>1) of the carrier gas flow at the outlet 7 of the Laval nozzle 3 results in a reduced gas pressure at the outlet 7 of the Laval nozzle 3. Therefore, the carrier gas flow carries away gas particles (i.e. ions, electrons, molecules) out of the ionization chamber 10, so that the gas pressure in the ionization chamber 10 is reduced thereby enhancing the efficiency of the plasma generation.

Further, the housing 9 comprises a connection 12 for connecting a vacuum meter or the like.

Figure 2:
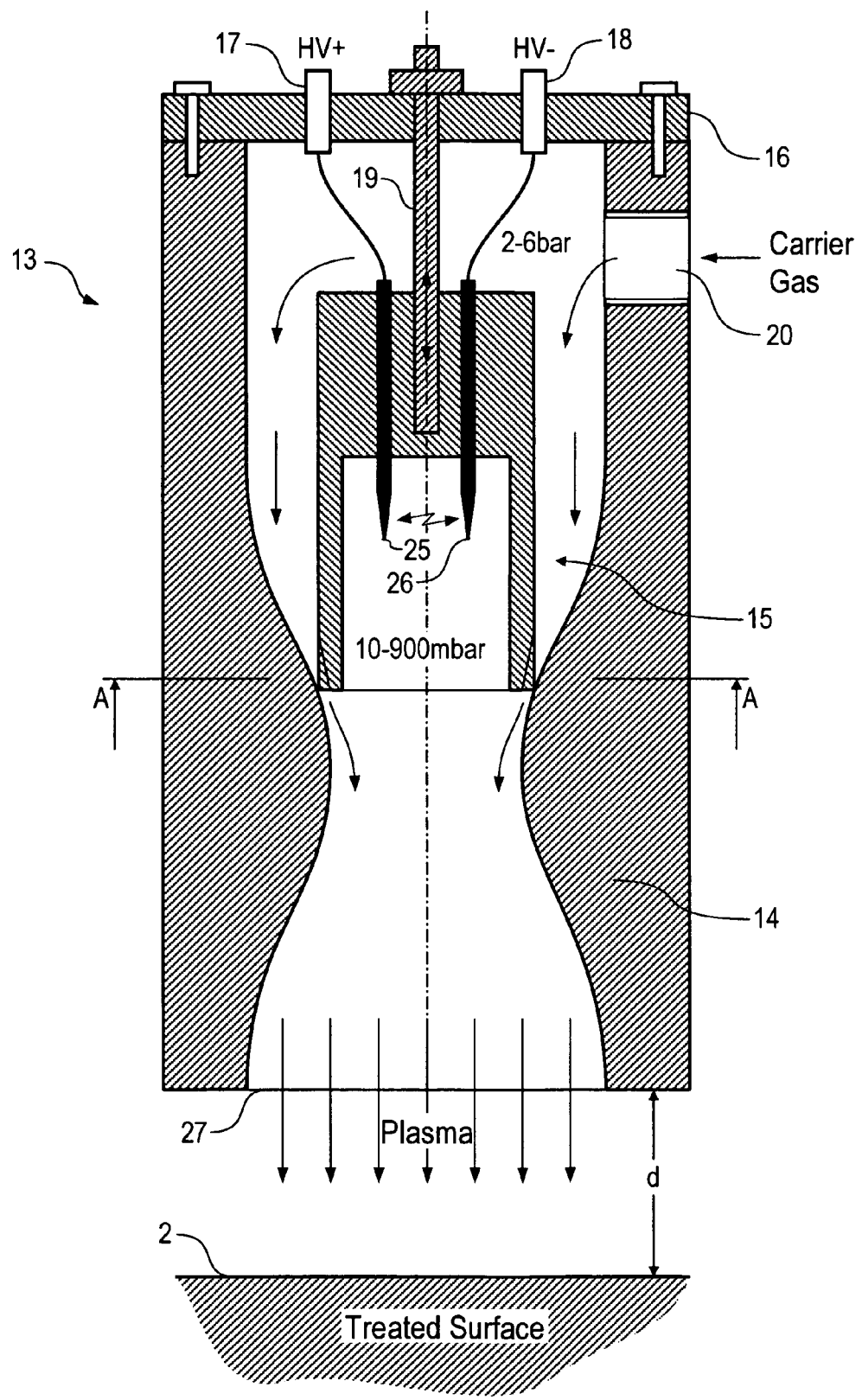
FIG. 2 is a cross sectional view of another embodiment of a plasma source according to the invention comprising a nozzle and a cup-shape ionization chamber within the nozzle.

FIG. 2 shows a cross section of another embodiment of a plasma source 13 according to the invention.

The plasma source 13 comprises a Laval nozzle 14 and a cup-shaped ionization chamber 15, which is disposed coaxially within the Laval nozzle 14.

Further, the plasma source 13 comprises a cover plate 16, which is screwed on the upper front side of the Laval nozzle 14. In the cover plate 16, there are ducts for high voltage contacts 17, 18, which can be connected to a plasma generator. Further, the cover plate 16 comprises a duct for a rod 19 supporting the ionization chamber 15. The rod 19 is fixed by a screw, so that the rod 19 can be adjusted axially in the direction of the arrow in order to adjust the axial position of the ionization chamber 15 within the Laval nozzle 14.

Further, the Laval nozzle 14 comprises an inlet 20 for introducing a carrier gas flow into the Laval nozzle 14.

The carrier gas flows within a ring-shaped gap between the outer wall of the ionization chamber 15 and the inner wall of the Laval nozzle 14 up to the downstream end of the ionization chamber 15, where the ionization chamber touches the inner wall of the Laval nozzle 14.

Therefore, the ionization chamber 15 comprises notches 21-24 (see FIG. 11), which are arranged in the outer wall of the ionization chamber 15 at the downstream end of the ionization chamber 15, so that the carrier gas can flow through the notches 21-24.

Further, the ionization chamber 15 comprises two electrodes 25, 26, which are connected to the high voltage contacts 17, 18, so that an excitation takes place between the electrodes 25, 26, which is illustrated by the arrow.

It should further be noted that the carrier gas flowing through the notches 21-24 produces a pressure reduction at the downstream end of the ionization chamber 15, so that the carrier gas flow carries away gas particles out of the inside of the ionization chamber 15 thereby reducing the gas pressure within the ionization chamber 15, which enhances the plasma efficiency.

Further, the plasma source 13 comprises an outlet 27 at its downstream end for applying the plasma to the surface of the object 2.

Figure 3:
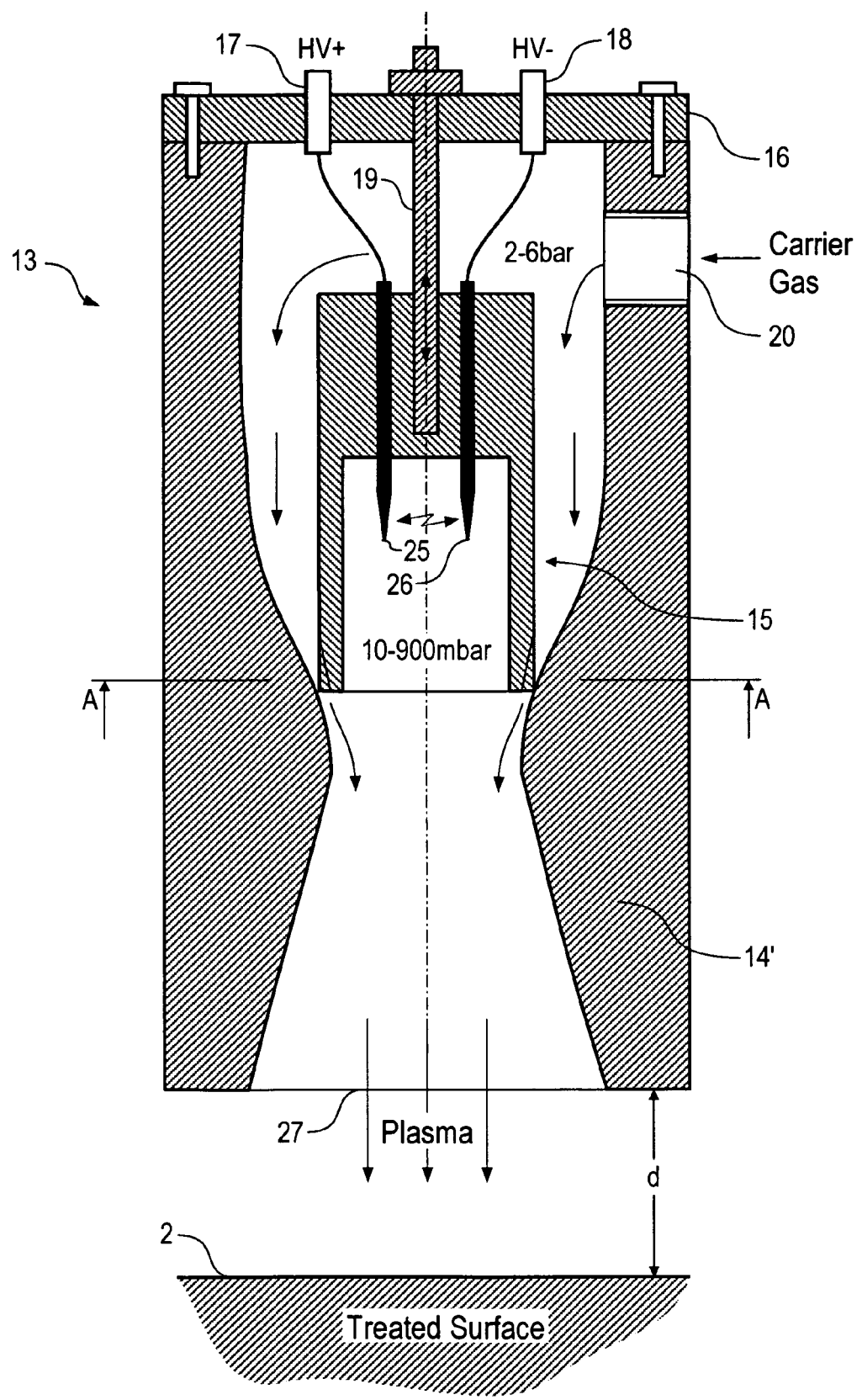
FIG. 3 is a modification of the embodiment according to FIG. 3, wherein the nozzle comprises a conically widening outlet.

FIG. 3 shows a modification of the plasma source 13 comprising a conduit pipe 14' instead of the Laval nozzle 14. The conduit pipe 14' comprises a cylindrical upstream portion, a conically widening downstream portion and a tapering middle portion.

Figure 4:
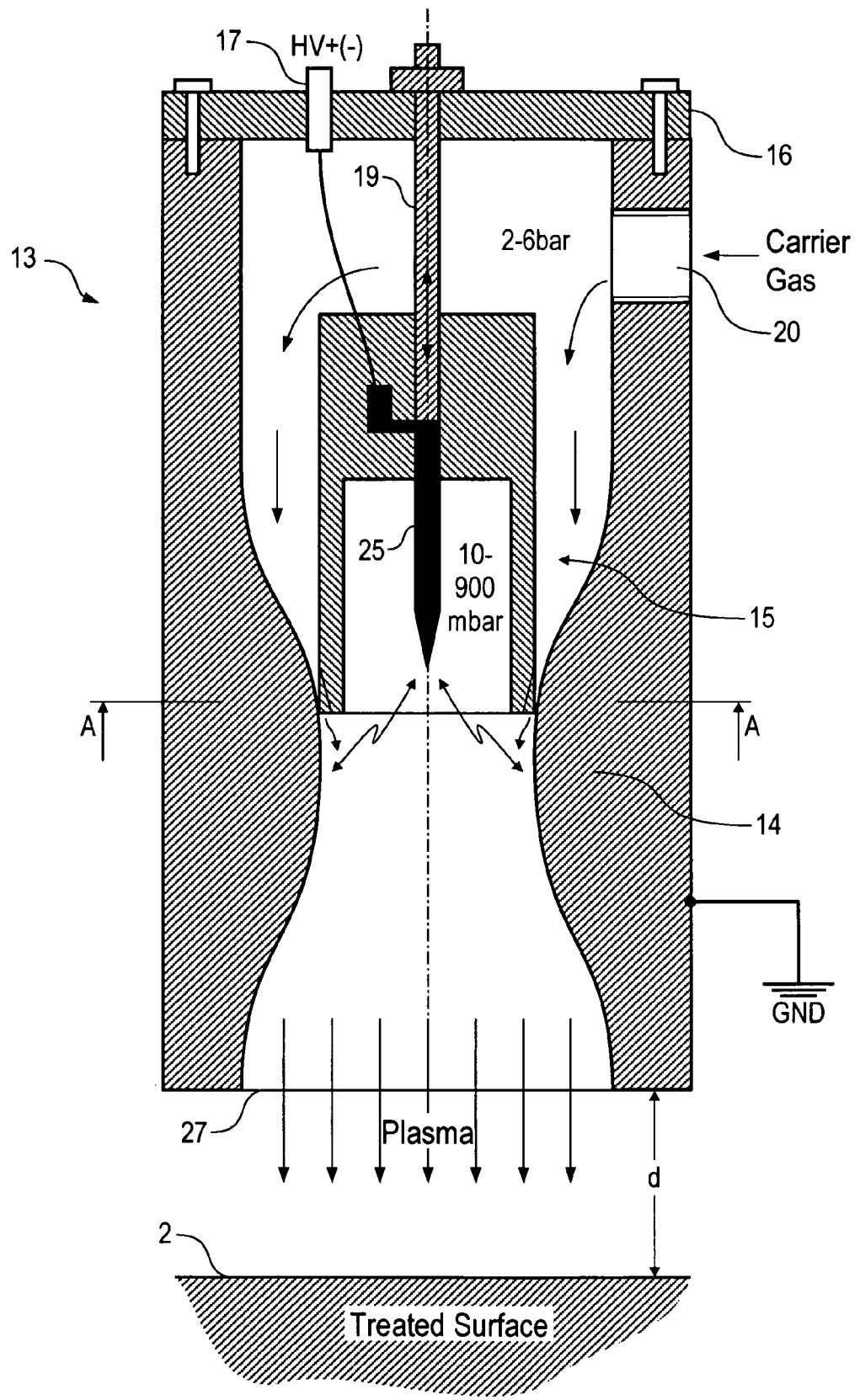
FIG. 4 is a sectional view of a modification of FIG. 3, wherein a single electrode is disposed within the ionization chamber.

FIG. 4 shows a modification of the embodiment of FIG. 2, which is characterized in that there is only the single electrode 25 in the ionization chamber 15, whereas the Laval nozzle 14 acts as a counter electrode and is therefore made of an electrically conductive material.

It should further be noted that the plasma is generated within the ionization chamber 15.

Figure 5:
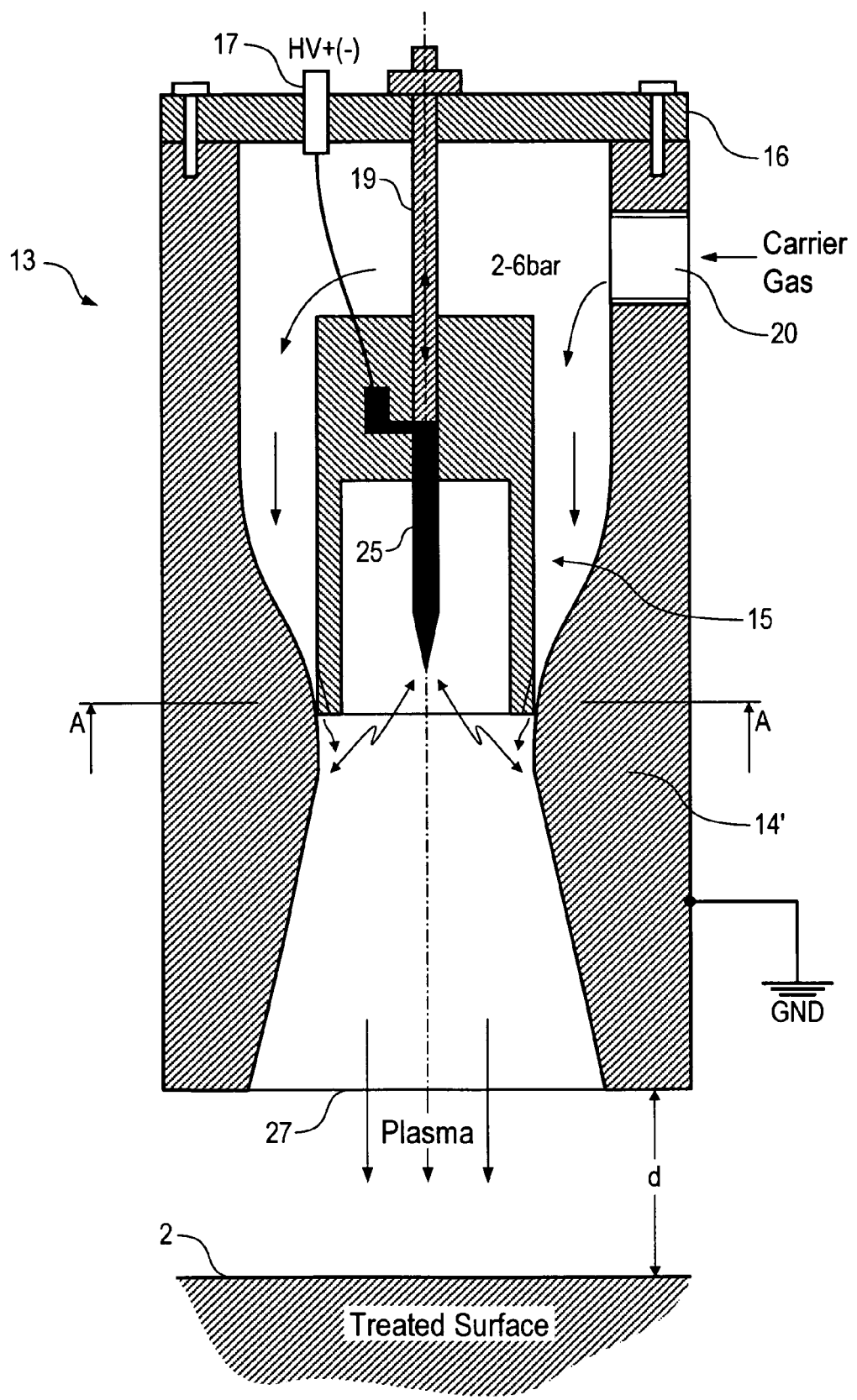
FIG. 5 is a sectional view of a modification of the embodiment according to FIG. 4, wherein the nozzle comprises a conically widening outlet.

FIG. 5 is a modification of the embodiment of FIG. 4, which is characterized in that the Laval nozzle 14 is replaced by the conduit pipe 14' as in FIG. 3.

Figure 6:
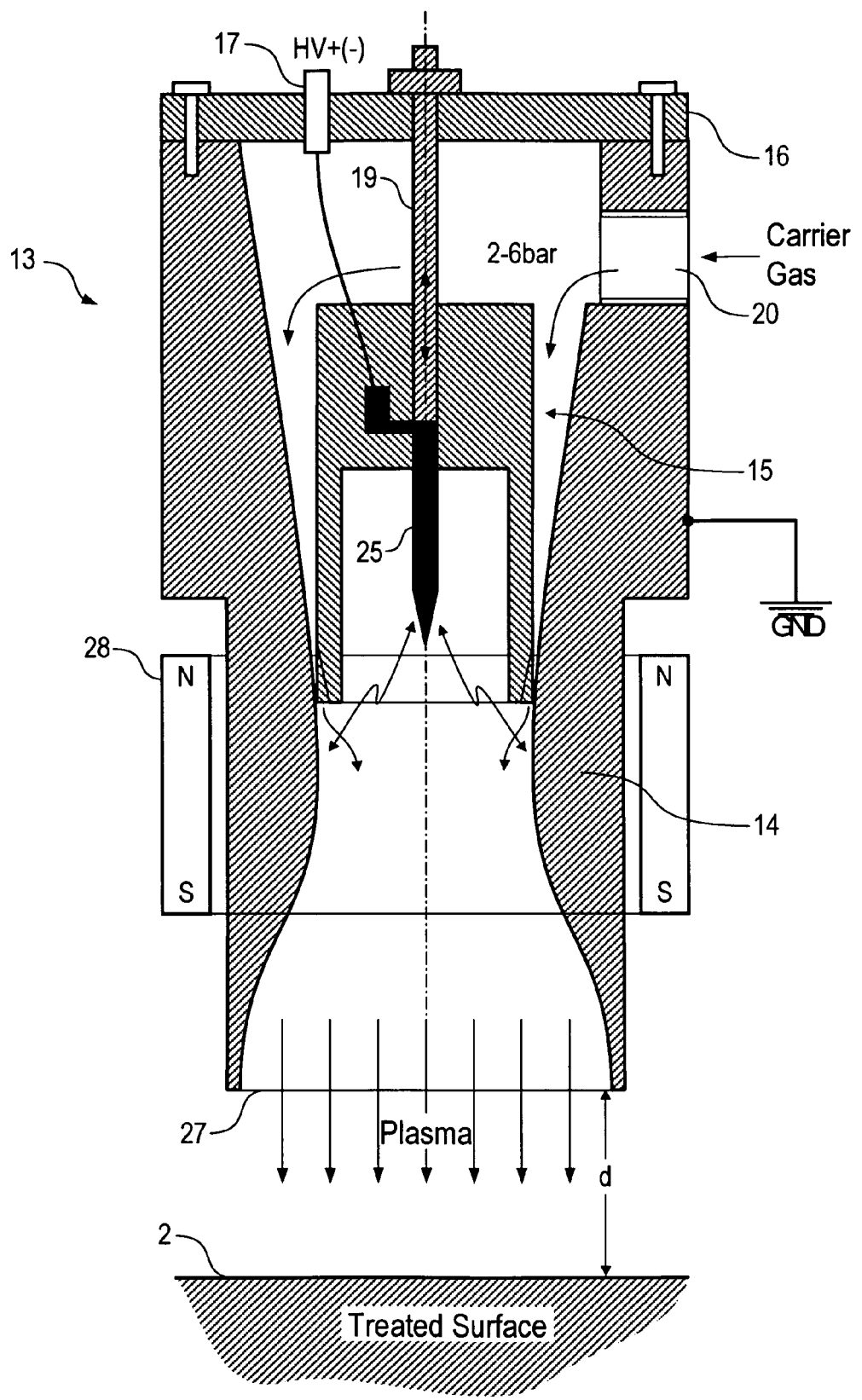
FIG. 6 is a sectional view of a modification of the embodiment according to FIG. 4, wherein a magnet is surrounding the nozzle generating a magnetic field within the nozzle.

FIG. 6 is a modification of the embodiment according to FIG. 5, which is characterized in that the Laval nozzle 14 is surrounded by a magnet 28, which is generating a coaxially aligned magnetic field within the bottleneck of the Laval nozzle 14 thereby enhancing the plasma generation.

Figure 7:
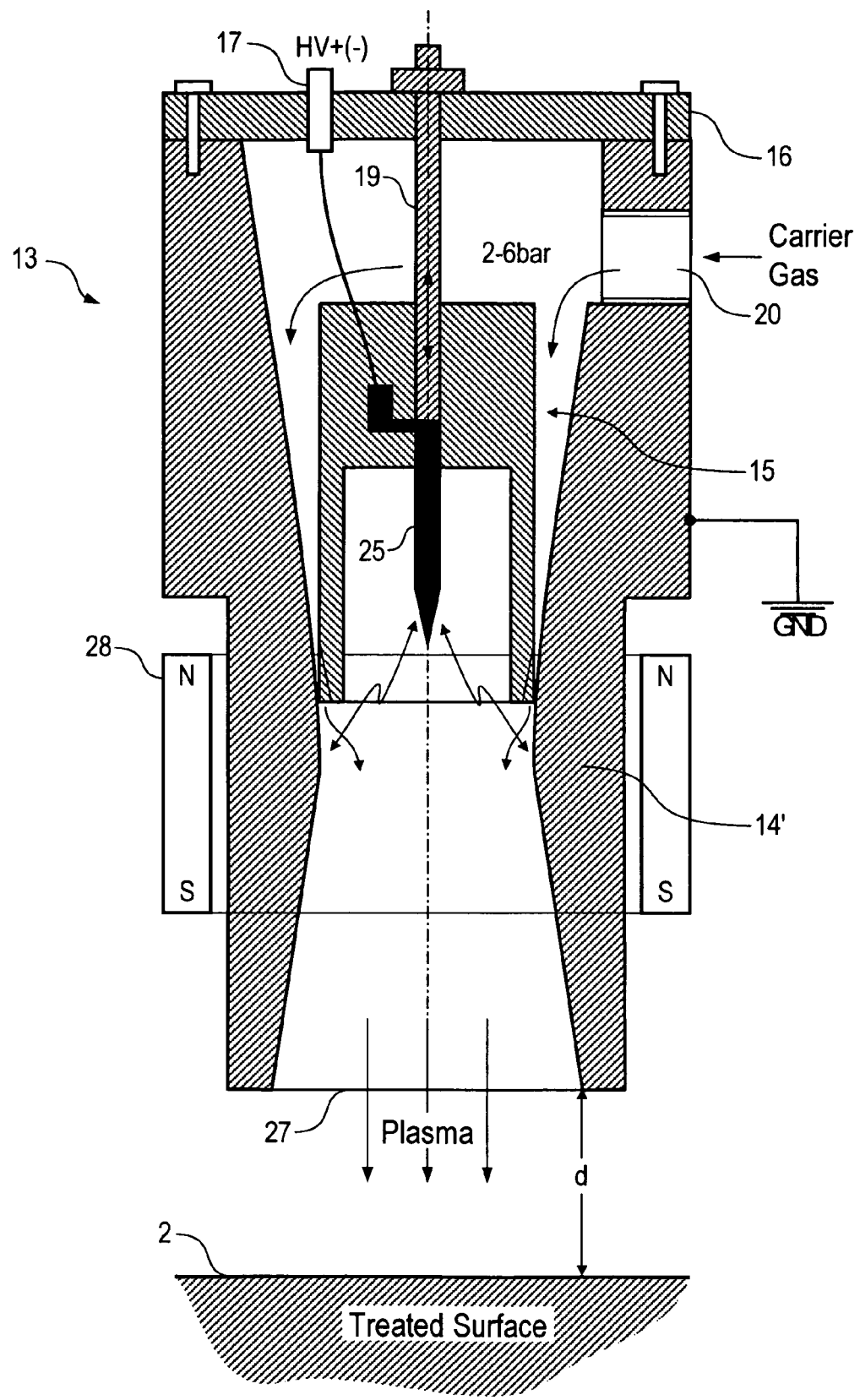
FIG. 7 is a modification of the embodiment according to FIG. 6, wherein the nozzle comprises a conically widening outlet.

FIG. 7 is a modification of the embodiment according to FIG. 6, which is characterized in that the Laval nozzle 14 is replaced by the conduit pipe 14' as mentioned above.

Figure 8:
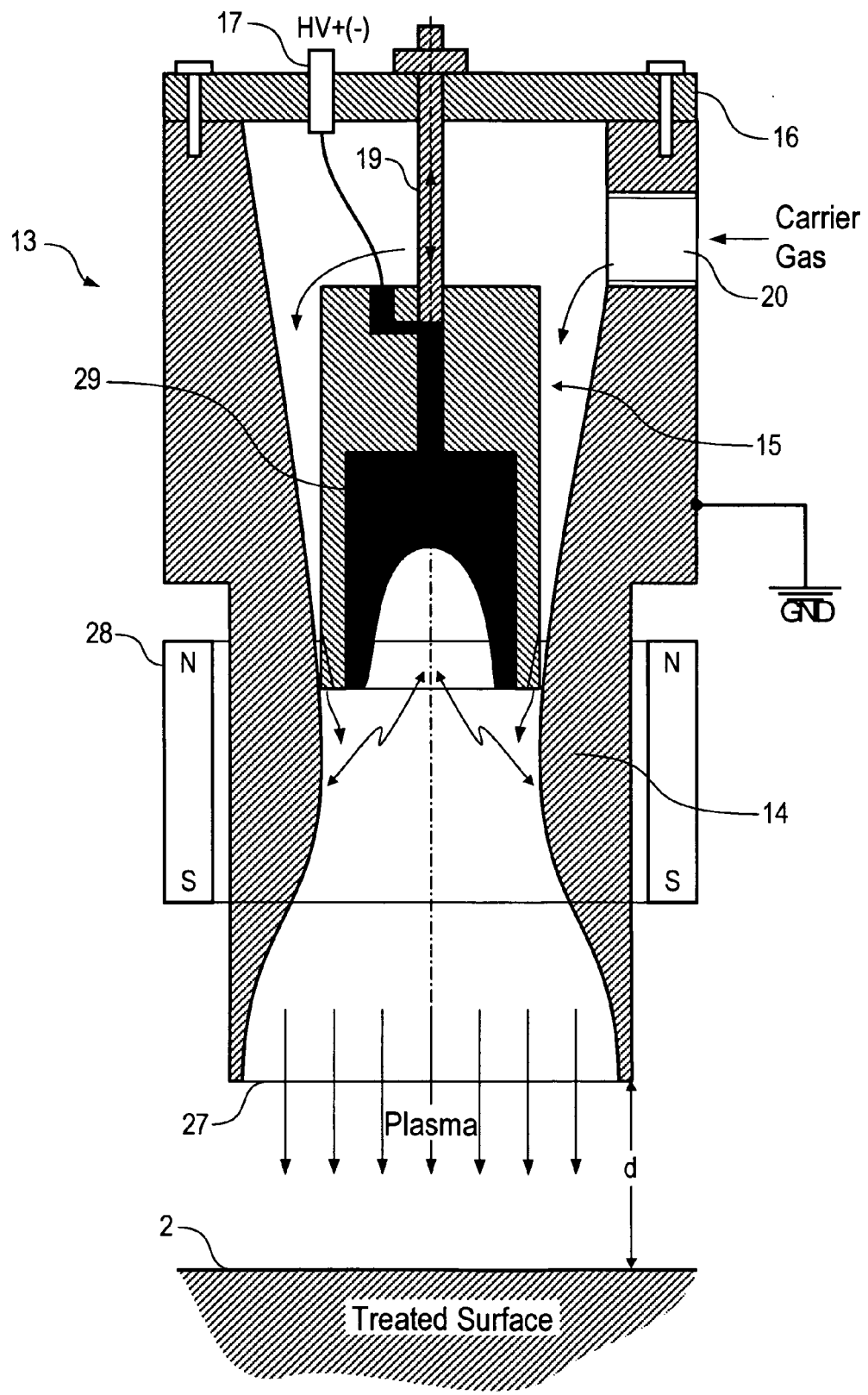
FIG. 8 is a modification of the embodiment according to FIG. 6 comprising a hollow cathode for plasma generation.

FIG. 8 is a modification of the embodiment according to FIG. 6, which is characterized in that there is a single hollow cathode 29 disposed within the ionization chamber 15, which enhances the plasma generation.

Figure 9:
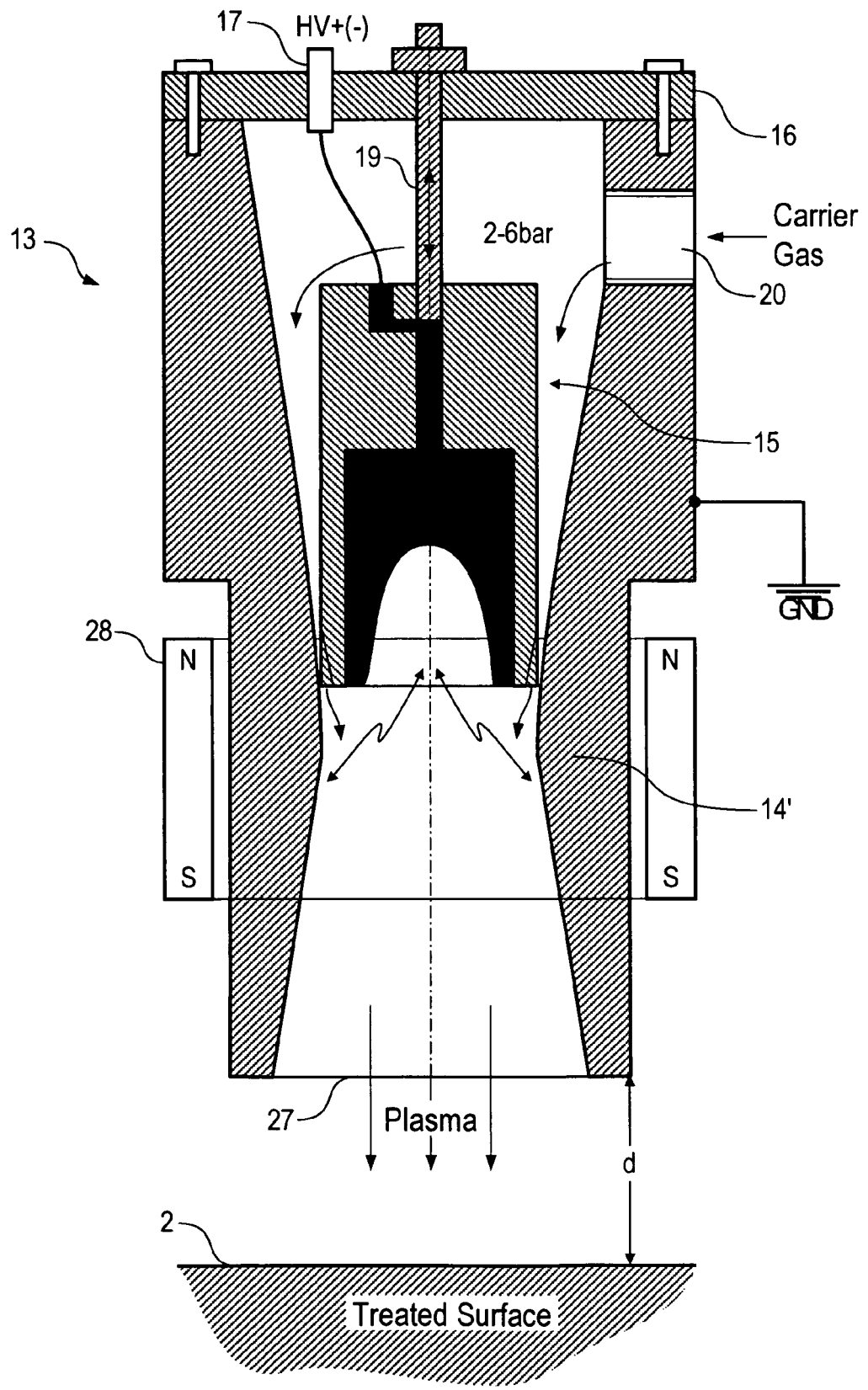
FIG. 9 is a cross sectional view of a modification of the embodiment according to FIG. 8, wherein the nozzle comprises a conically widening outlet.

FIG. 9 is a modification of the embodiment of FIG. 8, which is characterized in that the outlet is conically widening.

Figure 10:
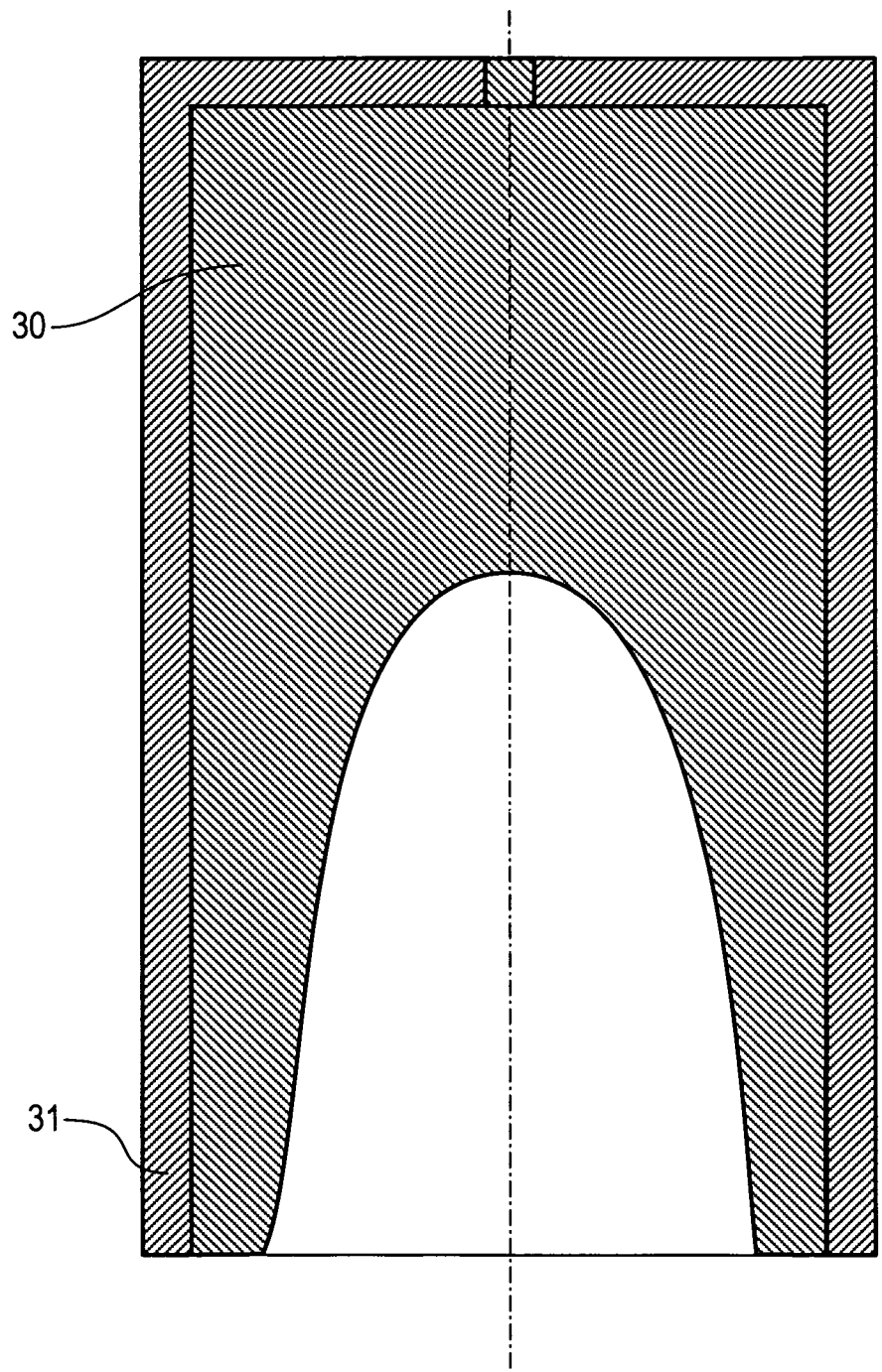
FIG. 10 is an enlarged cross sectional view of the hollow cathode for plasma generation.

FIG. 10 shows a cross sectional view of another embodiment of an ionization chamber 30 forming a hollow cathode. The ionization chamber 30 consists of an electrically conductive material and comprises an electrically insulating housing 31.

Figure 11:
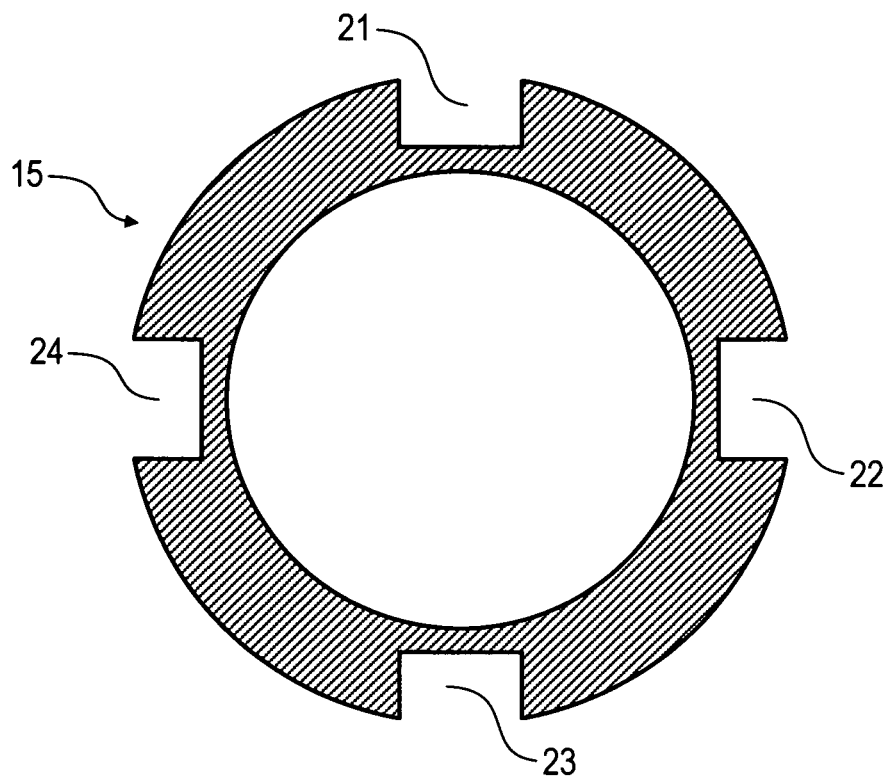
FIG. 11 is a cross sectional view of the ionization chamber along the line A-A in FIG. 2.

FIG. 11 shows a cross section of the ionization chamber 15 along the line A-A as shown in the afore-mentioned figures. It is illustrated that the ionization chamber 15 comprises notches 21-24 at its downstream end.

Figure 12:
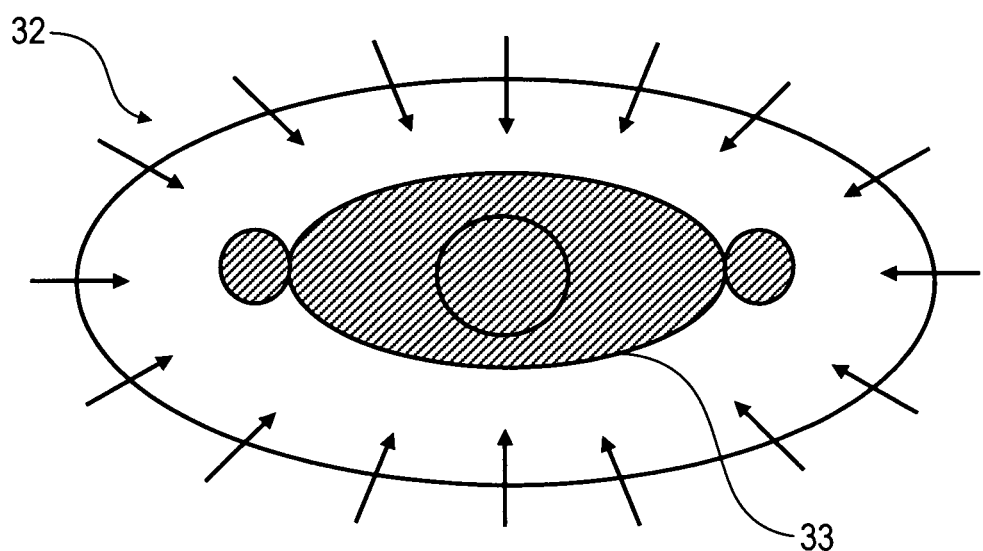
FIG. 12 is a schematic view of a medical device for treatment of a patient with plasma.

FIG. 12 shows a medical device 32 for treatment of a patient 33 with non-thermal plasma. In this embodiment, there are several plasma sources arranged around the patient 33, so that the plasma is applied to the patient 33 from different sides.

Figure 13:
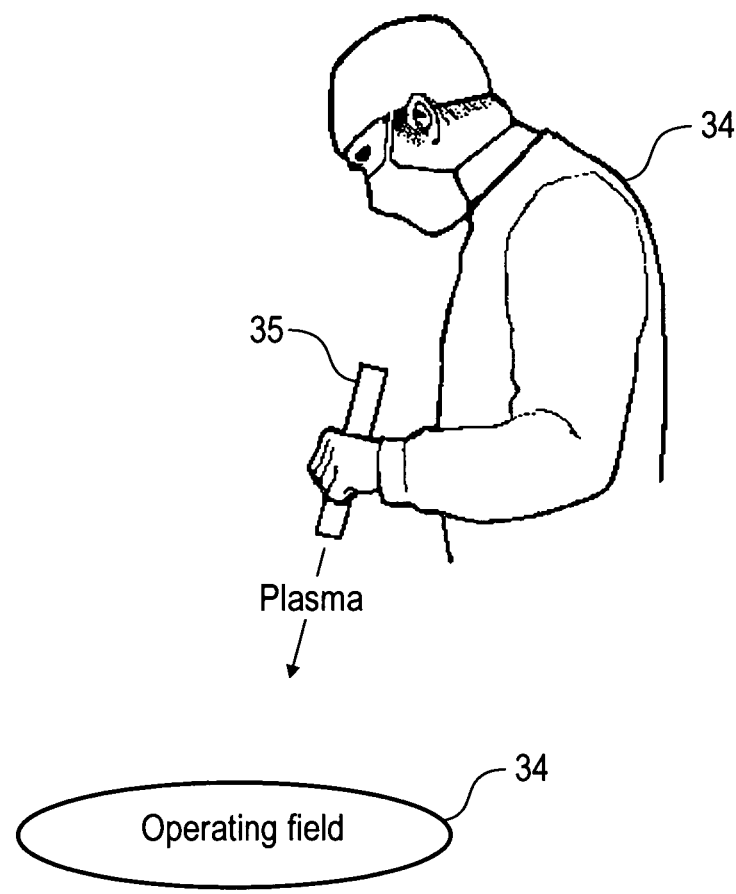
FIG. 13 is a schematical view showing a surgeon using the plasma source as a cauterizer.

Further, FIG. 13 shows a surgeon 34 handling a cauterizer 35 for cauterizing tissue in an operating field 36. In this embodiment, the cauterizer 35 comprises a plasma source as described above.

Figure 14:
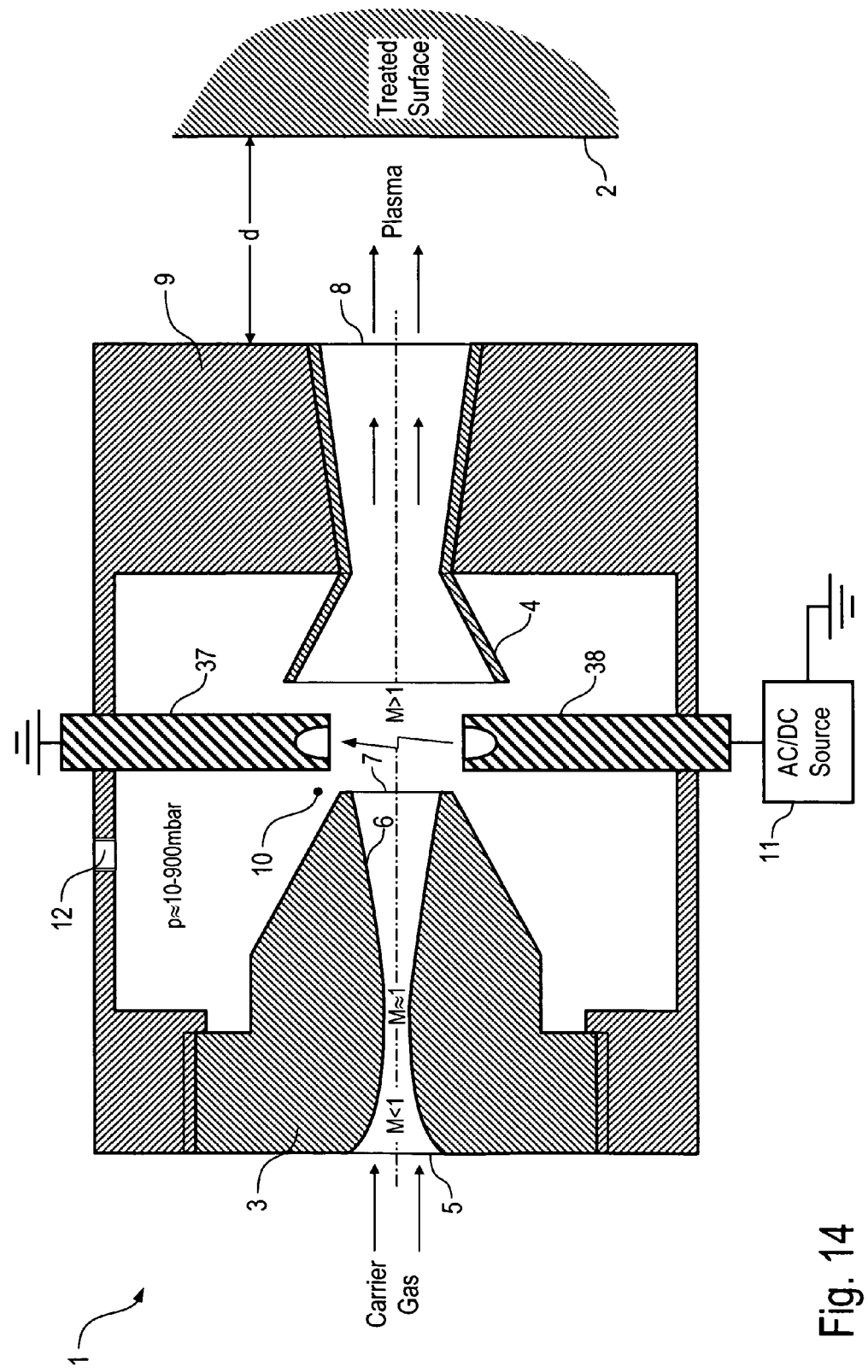
FIG. 14 is a schematical view showing a plasma source similar to the one of FIG. 1 but with a different electrode arrangement.

FIG. 14 is a modification of the embodiment of FIG. 1 so that reference is made to the above description relating to FIG. 1.

However, the Laval nozzle 3 and the conduit pipe 4 are not connected to the plasma generator 11. Instead, there are two electrodes 37, 38 for the excitation of the plasma in the ionization chamber 10.

The electrodes 37, 38 are radially aligned and arranged in a plane perpendicular to the gas flow between the Laval nozzle 3 and the conduit pipe 4.

The electrode 37 is connected to ground and the electrode 38 is connected to the plasma generator 11, which is an AC/DC source.

Figure 15:
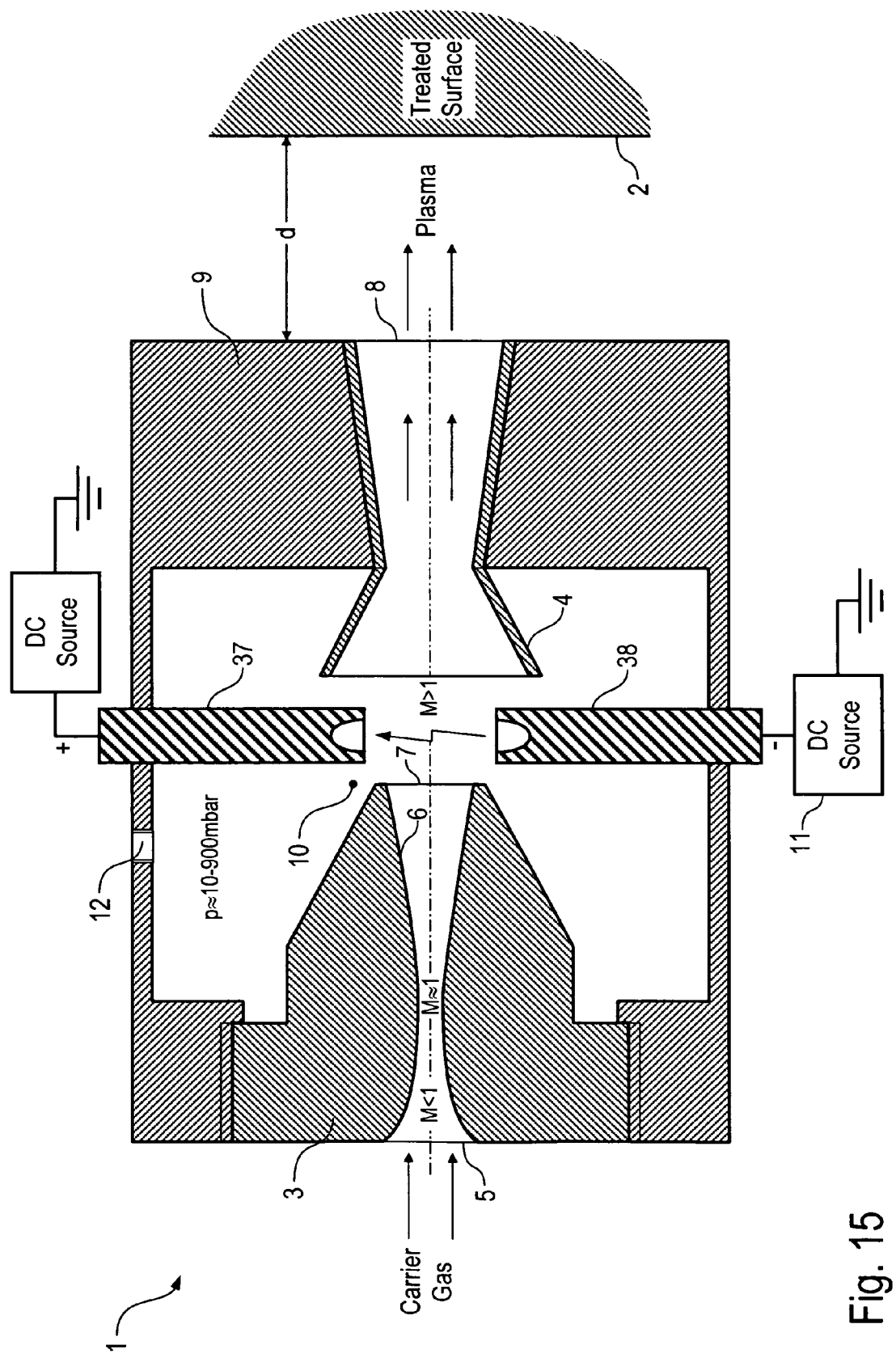
FIG. 15 is a modification of the embodiment of FIG. 14 comprising two DC sources for generating the plasma.

FIG. 15 is a modification of the embodiment of FIG. 14 so that reference is made to the above description relating to FIG. 14.

However, there are two plasma generators 11 in the form of DC sources, which are connected to the electrodes 37, 38.

Figure 16:
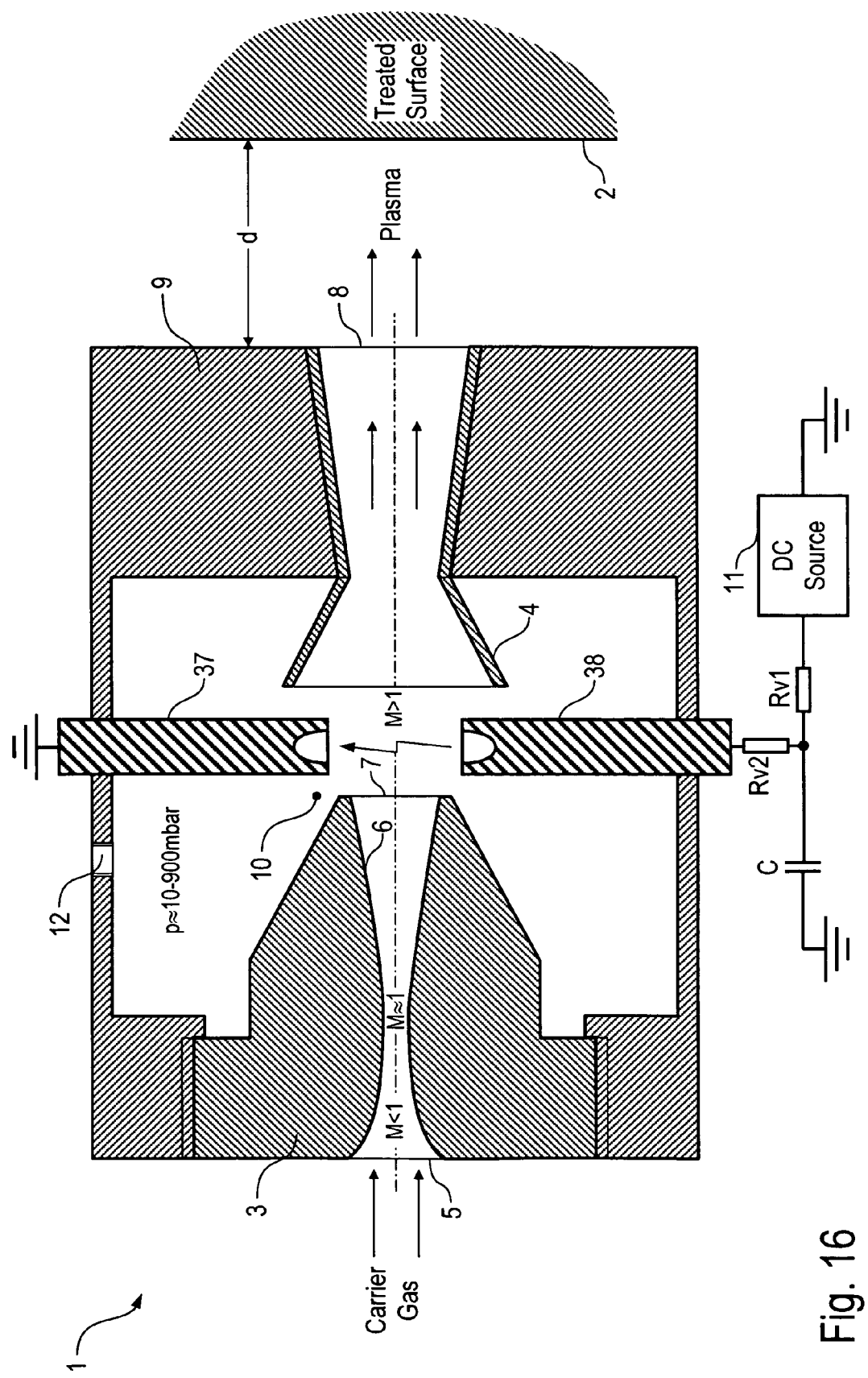
FIG. 16 is a modification of the embodiment of FIG. 14 comprising a free-running pulsed plasma excitation.

FIG. 16 is a modification of the embodiment of FIG. 14 so that reference is made to the above description relating to FIG. 14.

However, there is a free-running pulsed plasma excitation. Therefore, the plasma generator 11 in the form of a DC source is connected to the electrode 38 via two resistors Rv1≈1 MΩ, Rv2≈1Ω-100 kΩ and a capacitor C=1 nF which is connected to ground. The plasma generator 11 generates a high voltage of about U≈6 kV resulting in a charge time $\tau_{CHARGE}$≈1 ms, a discharge frequency $f_{DISCHARGE}$≈1 kHz and pulse duration $\tau_{PULSE}$≈1 ns-10 ms.

Figure 17:
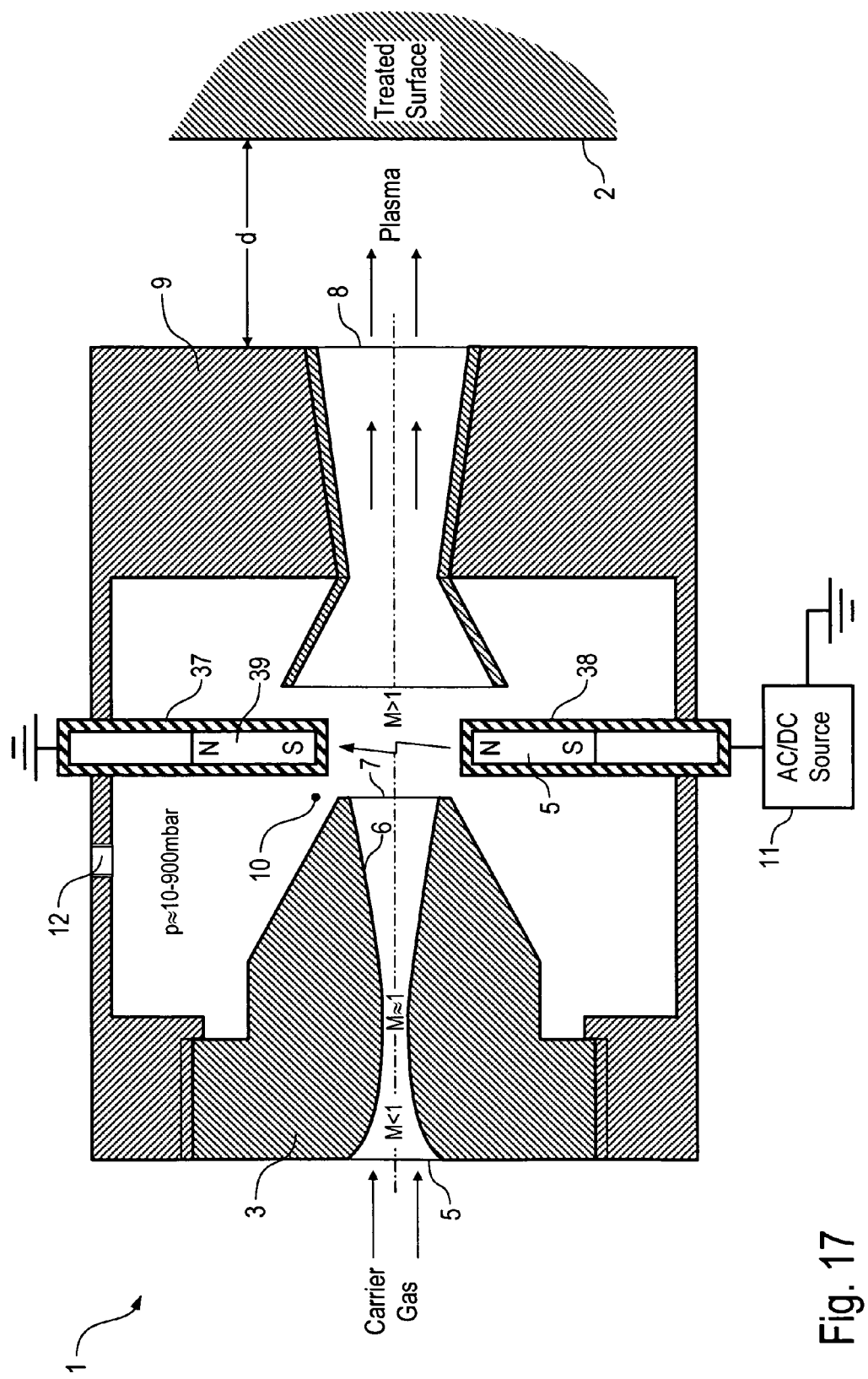
FIG. 17 is a schematical view showing a plasma source similar to the one of FIG. 15 but with an additional magnet.

FIG. 17 is a modification of the embodiment of FIG. 14 so that reference is made to the above description relating to FIG. 14.

One distinct feature of this embodiment is that there are permanent magnets 39, 40 being integrated into the electrodes 37, 38. The permanent magnets 39, 40 generate a magnetic field in the ionization chamber 10 thereby improving the plasma generation.

Figure 18:
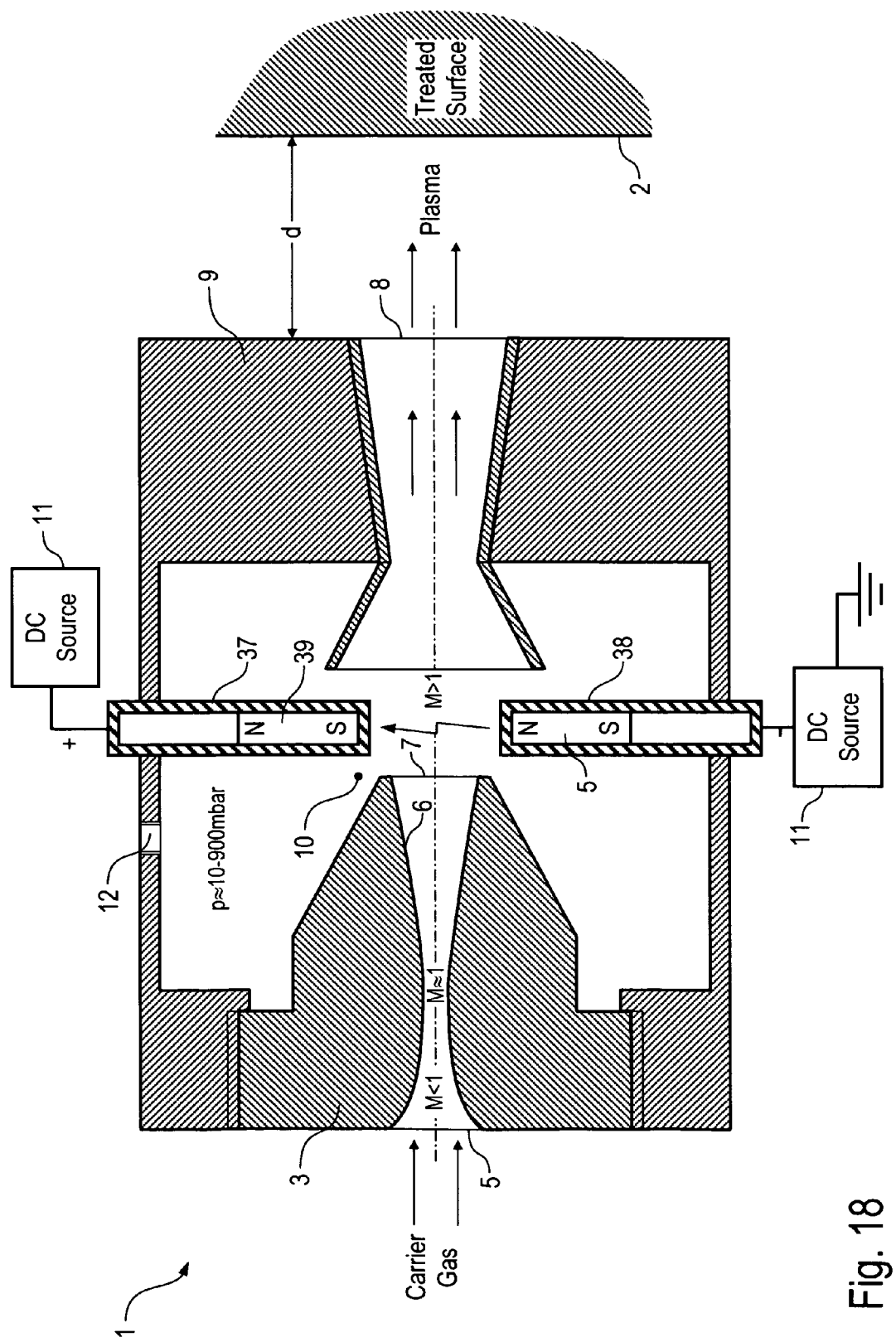
FIG. 18 is a modification of the embodiment of FIG. 17 comprising two DC sources for generating the plasma.

FIG. 18 is a modification of the embodiment of FIG. 17 so that reference is made to the above description relating to FIG. 17.

However, there are two plasma generators 11 in the form of DC source, which are connected to the electrodes 37, 38.

Figure 19:
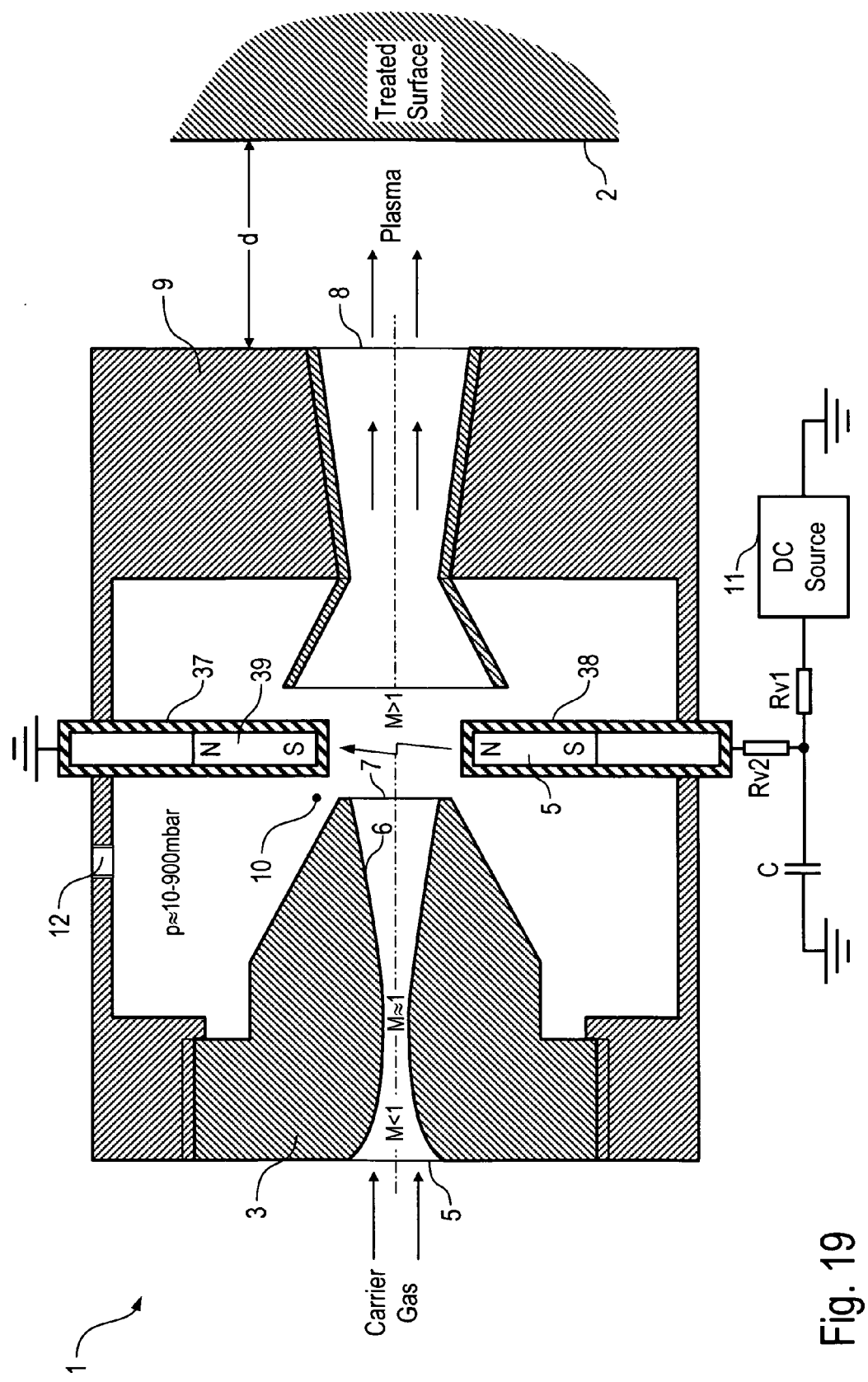
FIG. 19 is a modification of the embodiment of FIG. 17 comprising a free-running pulsed plasma excitation.

Finally, FIG. 19 is a modification of the embodiment of FIG. 17 so that reference is made to the above description relating to FIG. 17.

However, there is a free-running pulsed plasma excitation. Therefore, the plasma generator 11 in the form of a DC source is connected to the electrode 38 via two resistors Rv1, Rv2 and a capacitor C which is connected to ground.

Although the invention has been described with reference to the particular arrangement of parts, features and the like, these are not intended to exhaust all possible arrangements of features, and indeed many other modifications and variations will be ascertainable to those of skill in the art.

LIST OF REFERENCE NUMERALS

1 Plasma source
2 Object
3 Laval nozzle
4 Conduit pipe
5 Inlet
6 Inner wall
7 Outlet
8 Outlet
9 Housing
10 Ionization chamber
11 Plasma generator
12 Connection
13 Plasma source
14 Laval nozzle
14' Conduit pipe
15 Ionization chamber
16 Cover plate
17, 18 High voltage contacts
19 Rod
20 Inlet
21-24 Notches
25, 26 Electrodes
27 Outlet
28 Magnet
29 Hollow cathode
30 Ionization chamber
31 Housing
32 Medical device 33 Patient
34 Surgeon
35 Cauterizer
36 Operating field
37 Electrode
38 Electrode
39 Permanent magnet
40 Permanent magnet

The invention claimed is:

1. A plasma source for generating a low temperature plasma, comprising:
   a) a conduit carrying a gas flow, the conduit comprising a nozzle arranged upstream of an ionization chamber, the conduit further comprising a conduit pipe arranged downstream of the ionization chamber, wherein an upstream end of the nozzle comprises an inlet for introducing a gas flow into the nozzle, and wherein the conduit pipe comprises an outlet at a downstream end thereof;
   b) a housing encasing the nozzle and the conduit pipe and defining the ionization chamber between the nozzle and the conduit pipe; and
   c) a plasma generator adapted to generate a low temperature plasma in the ionization chamber between the nozzle and conduit pipe,
   wherein: (i) the nozzle and the conduit pipe are arranged to reduce a pressure in the ionization chamber when the gas flow is carried by the conduit; and (ii) the outlet is arranged for applying the plasma to a surface.

2. The plasma source according to claim 1, wherein the nozzle is a Venturi nozzle.

3. The plasma source according to claim 1, wherein the nozzle is a Laval nozzle.

4. The plasma source according to claim 1, wherein the plasma source is adapted to generate:
   (1) a subsonic flow speed of the gas flow in the conduit upstream of the nozzle;
   (2) a supersonic flow speed of the gas flow in the conduit downstream of the nozzle; and
   (3) a substantially sonic flow speed of the gas flow in the nozzle.

5. The plasma source according to claim 1, wherein the ionization chamber is ring-shaped and surrounds the conduit.

6. The plasma source according to claim 5, wherein the plasma source is adapted to generate a ring-shaped plasma discharge within the ionization chamber, wherein the plasma discharge surrounds the conduit.

7. The plasma source according to claim 1, wherein:
   the ionization chamber is cup-shaped and open in flow-direction, and
   the ionization chamber is disposed within the conduit.

8. The plasma source according to claim 7, wherein the cup-shaped ionization chamber comprises an axial position, which is adjustable in an axial direction.

9. The plasma source according to claim 1, further comprising a first electrode and a second electrode for generating the low temperature plasma in the ionization chamber.

10. The plasma source according to claim 9, wherein:
    the first electrode is formed by the nozzle of the conduit; and
    the second electrode is formed by a conic part of the conduit, wherein the conic part is tapering in flow direction and surrounding the nozzle.

11. The plasma source according to claim 9, wherein the first electrode and the second electrode are both disposed within the ionization chamber.

12. The plasma source according to claim 9, wherein:
    the first electrode is formed by the conduit; and
    the second electrode is disposed alone in the ionization chamber.

13. The plasma source according to claim 1, wherein at least one of (a) the ionization chamber, or (b) the housing comprises an electrically conductive material in order to reduce microwave irradiation of the plasma source.

14. The plasma source according to claim 13, wherein there is no direct radiation path from an inside of the ionization chamber into the conduit and through the outlet of the conduit, so that the plasma source is substantially free of plasma generated electromagnetic irradiation.

15. The plasma source according to claim 1, wherein there is a direct radiation path from an inside of the ionization chamber into the conduit and through an outlet of the conduit, so that the plasma source emits plasma generated electromagnetic irradiation.

16. The plasma source according to claim 1, wherein the ionization chamber comprises walls, which are at least partially transparent thereby enabling a visual control of the plasma generation within the ionization chamber.

17. The plasma source according to claim 16, wherein the ionization chamber comprises a window made from a material, which is transparent for visible light and non-transparent for ultraviolet light.

18. The plasma source according to claim 1, wherein the ionization chamber comprises a connection for connecting a vacuum meter.

19. The plasma source according to claim 1, further comprising a magnet generating a magnetic field in the ionization chamber or downstream of the ionization chamber in the conduit, wherein said magnetic field enhances the plasma generation.

20. The plasma source according to claim 1, wherein the plasma source is adapted to generate a vacuum in the ionization chamber in a range from 5 mbar to 900 mbar.

21. The plasma source according to claim 1, wherein the plasma source is adapted to receive a gas selected from the group consisting of ambient air, nitrogen, noble gas and argon, wherein the gas optionally contains additives.

22. The plasma source according to claim 1, wherein the plasma source is adapted to receive the gas flow in the conduit in amounts less than a value selected from the group consisting of 50 l/min, 40 l/min, 30 l/min, 20 l/min and 10 l/min.

23. The plasma source according to claim 1, wherein the plasma generator is adapted for a direct current excitation.

24. The plasma source according to claim 1, wherein the plasma generator is adapted for an alternating current excitation.

25. The plasma source according to claim 1, wherein the plasma source is adapted to generate the plasma having a temperature of less than a temperature value selected from the group consisting of 100° C., 75° C., 50° C., 40° C. and 30° C.

26. The plasma source according to claim 1, wherein the conduit is adapted to carry away in the gas flow the following gas particles out of the ionization chamber:
    a) molecules;
    b) atoms;
    c) ions; and
    d) electrons.

27. A medical device, comprising a plasma source according to claim 1.

28. The medical device according to claim 27, wherein the medical device is a sterilizer.

29. The medical device according to claim 27, wherein the medical device is a cauterizer.

30. A method of treating an object, said method comprising:
   providing a plasma source according to claim 1; and
   applying to the object a plasma generated by the plasma source to treat the object.

31. The method of claim 30, wherein the treating comprises decontaminating the object.

32. The method according to claim 31, wherein the object is a member selected from the group consisting of:
   a) an electronic circuit,
   b) an electric component,
   c) an electronic component,
   d) a component of a spacecraft,
   e) a subassembly of a spacecraft, and
   f) a space-suit.

33. The method of claim 30, wherein the object is a patient and the treating comprises cauterizing and/or sterilizing a wound of the patient.

* * * * *